United States Patent
Mathad et al.

(10) Patent No.: US 9,139,537 B2
(45) Date of Patent: Sep. 22, 2015

(54) PROCESS FOR PREPARATION OF BOSENTAN

(75) Inventors: Vijayavitthal Thippannachar Mathad, Maharashtra (IN); Navnath Chintaman Niphade, Maharashtra (IN); Kunal Madhav Jagtap, Maharashtra (IN); Chandrashekar Trimbak Gaikwad, Maharashtra (IN)

(73) Assignee: Megafine Pharma(P) Ltd., Mumbai, Maharashtra (IN)

( * ) Notice: Subject to any disclaimer, the term of this patent is extended or adjusted under 35 U.S.C. 154(b) by 188 days.

(21) Appl. No.: 13/816,376

(22) PCT Filed: Mar. 28, 2011

(86) PCT No.: PCT/IN2011/000209
§ 371 (c)(1), (2), (4) Date: Feb. 11, 2013

(87) PCT Pub. No.: WO2012/020421
PCT Pub. Date: Feb. 16, 2012

(65) Prior Publication Data
US 2013/0296560 A1    Nov. 7, 2013

(30) Foreign Application Priority Data
Aug. 11, 2010   (IN) .................. 2266/MUM/2010

(51) Int. Cl.
*C07D 403/04*   (2006.01)
*C07D 239/69*   (2006.01)
*C07D 239/52*   (2006.01)

(52) U.S. Cl.
CPC ............ *C07D 239/69* (2013.01); *C07D 239/52* (2013.01)

(58) Field of Classification Search
CPC .................................................. C07D 239/69
See application file for complete search history.

(56) References Cited

U.S. PATENT DOCUMENTS

| 5,292,740 A | 3/1994 | Burri et al. |
| 6,136,971 A | 10/2000 | Harrington et al. |

FOREIGN PATENT DOCUMENTS

| WO | WO-2009/004374 | 1/2009 |
| WO | WO-2009/083789 | 7/2009 |
| WO | WO-2009/093739 | 7/2009 |
| WO | WO-2009/095933 | 8/2009 |
| WO | WO-2009/112954 | 9/2009 |
| WO | WO-2010/032261 | 3/2010 |
| WO | WO 2010032261 A1 * | 3/2010 |
| WO | WO-2011/058524 | 5/2011 |

OTHER PUBLICATIONS

VWR International. "Safety Data Sheet" for ethylene glycol. (c) Nov. 25, 2002. Available from: < http://ncifrederick.cancer.gov/rtp/LASP/intra/forms/msds/msds_ethylene_glycol.pdf >.*
BioPharma-Reporter.com. "One-pot process for toxic APIs." (c) Dec. 8, 2004. Available from: < http://www.in-pharmatechnologist.com/Processing/One-pot-process-for-toxic-APIs >.*
MacMillan. "Phase-transfer catalysis." (c) Apr. 2008. Available from: < https://www.princeton.edu/chemistry/macmillan/group-meetings/AM_phase%20transfer%20catalysis.pdf >.*
"International Search Report in PCT/IN2011/000209", mailed on Aug. 16, 2011, 4 pages.

* cited by examiner

*Primary Examiner* — Noble Jarrell
*Assistant Examiner* — John S Kenyon
(74) *Attorney, Agent, or Firm* — Servilla Whitney LLC

(57) ABSTRACT

A novel ammonium salt of Bosentan of formula (VIII); has been disclosed. The salt may be either crystalline or amorphous or mixture of Crystalline and amorphous form. A novel single pot process for the preparations of ammonium salt of Bosentan has been disclosed. The process comprises reacting the 4,6-dichloro-5-(2-methoxyphenoxy)-2,2'-bipyrimidine with 4-tert-butylbenzenesulfonamide in the presence of solvent and a base; adding ethylene glycol to the reaction mass and isolating the ammonium salt of Bosentan. The ammonium salt of Bosentan is converted into Bosentan and further into Bosentan Monohydrate which are substantially free from dimer impurity and 6-hydroxy impurity.

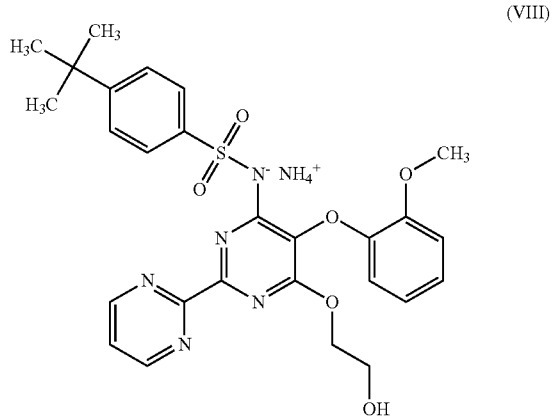

13 Claims, 6 Drawing Sheets

US 9,139,537 B2

PROCESS FOR PREPARATION OF BOSENTAN

CROSS-REFERENCE TO RELATED APPLICATIONS

Figure 1:
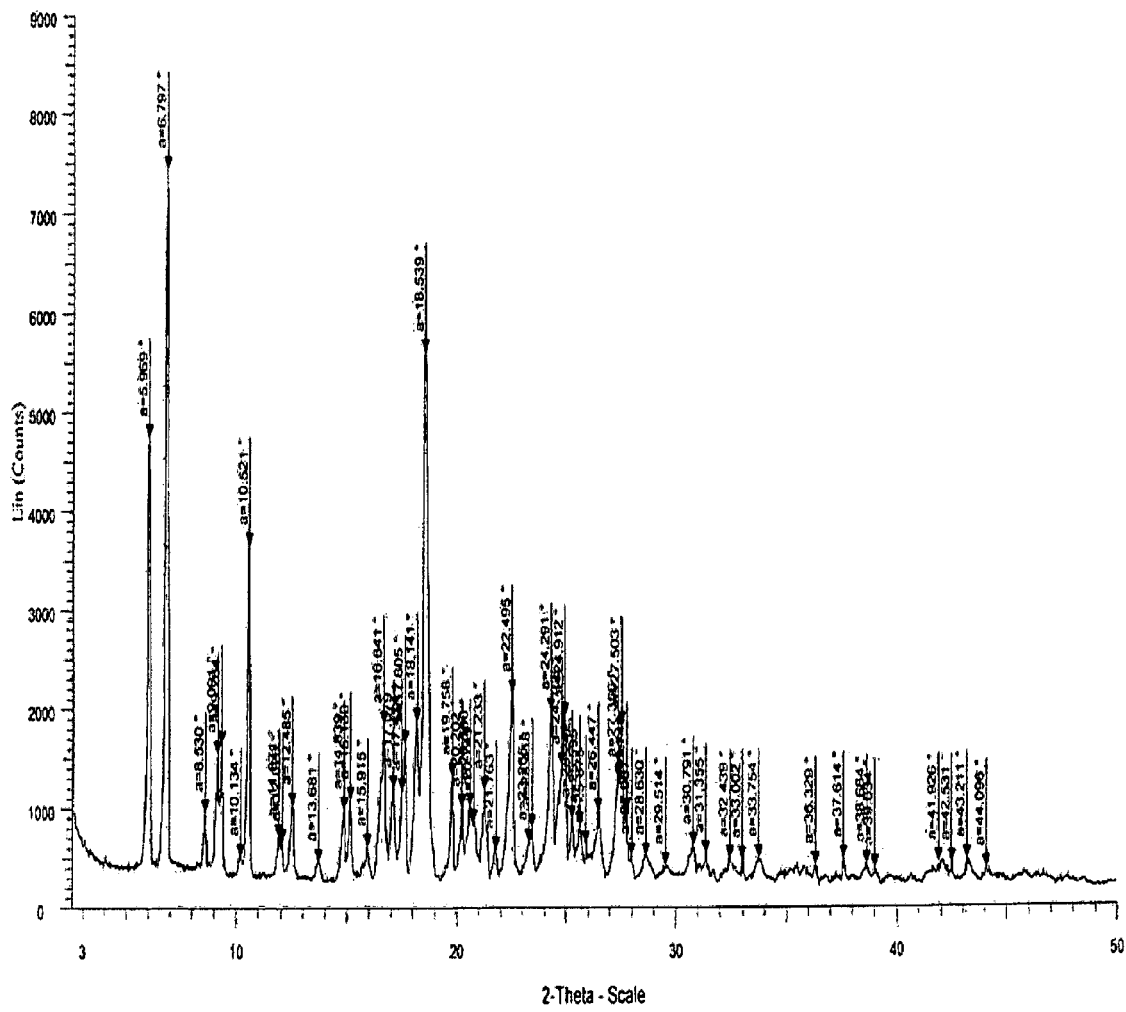

This application is a national stage entry of PCT/IN2011/000209, filed Mar. 28, 2011, which claims priority from Indian Patent Application no 2266/MUM/2010 filed on 11 Aug. 2010, both of which are incorporated herein by reference in their entireties.

FIELD

The present invention relates to a process for the preparation of Bosentan monohydrate of Formula (II);

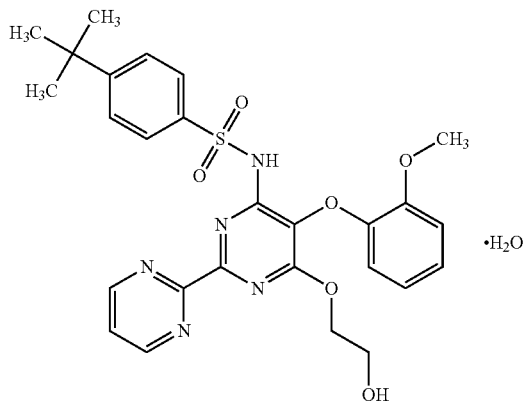

Formula (II)

wherein Bosentan Monohydrate of the formula (II) is substantially free from impurities.

The invention also relates to a process for the preparation of Bosentan of Formula (I);

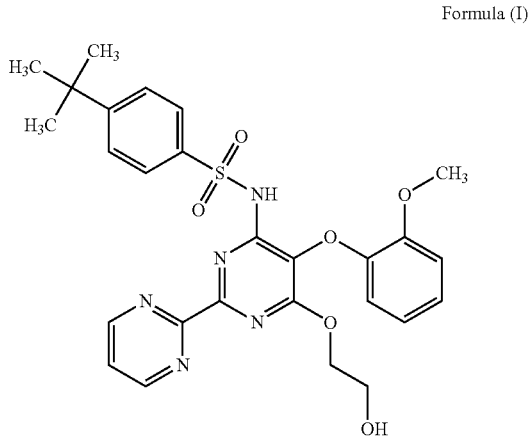 [SMILES: COc1ccccc1Oc1c(NS(=O)(=O)c2ccc(C(C)(C)C)cc2)nc(-c2ncccn2)nc1OCCO]

Formula (I)

wherein Bosentan of the formula (I) is substantially free from impurities.

The present invention also relates to novel ammonium salt of Bosentan of formula (VIII);

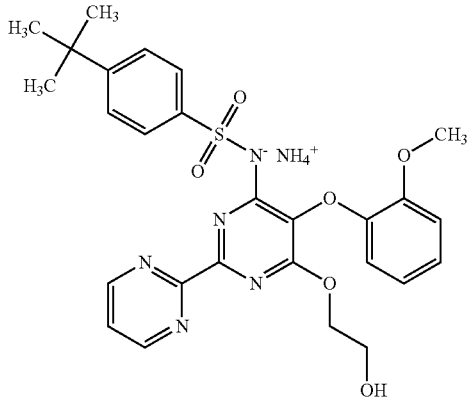

Formula (VIII)

The present invention also relates to a single pot process for the preparation of ammonium salt of Bosentan of the formula (VIII).

BACKGROUND

Bosentan is a dual endothelin receptor antagonist important in the treatment of pulmonary artery hypertension (PAH). The chemical name of Bosentan is p-tert-butyl-N-[6-(2-hydroxyethoxy)-5-(2-Methoxyphenoxy)-2-(2-pyrimidinyl)-4-pyrimidinyl]benzene sulfonamide and it is structurally represented by formula-(I). Bosentan Monohydrate is pharmaceutically active substance and marketed under the brand name TRACLEER® as immediate release tablets. Bosentan is a competitive antagonist of endothelin-1 at the endothelin-A (ET-A) and endothelin-B (ET-B) receptors. Under normal conditions, endothelin-1 binding of ET-A or ET-B receptors causes pulmonary vasoconstriction. By blocking this interaction, Bosentan decreases pulmonary vascular resistance. Bosentan has a slightly higher affinity for ET-A than ET-B.

U.S. Pat. No. 5,292,740 (hereinafter referred to as the '740 patent) discloses various sulfonamide derivatives, processes for their preparation, pharmaceutical compositions and methods of use thereof. Among them, Bosentan, p-tert-butyl-N-[6-(2-hydroxyethoxy)-5-(2-methoxyphenoxy)-2-(2-pyrimidinyl)-4-pyrimidinylbenzenesulfonamide Monohydrate, has a wide variety of biological activities including inhibiting the renin angiotensin system and acting as an endothelin antagonist. The process as disclosed in '740 is illustrated as Path A in Scheme-1. 5-(2-methoxyphenoxy)-2-(2-pyrimidin-2-yl)-4,6(1H,5H)-pyrimidinedione is reacted with phosphorous oxychloride in acetonitrile to obtain 4,6-dichloro-5-(2-methoxyphenoxy)-2,2'-bipyrimidine, which is further condensed with 4-tert-butylbenzenesulfonamide potassium in dimethylsulfoxide followed by treatment with hydrochloric acid to obtain p-tert-butyl-N-[6-chloro-5-(2-methoxyphenoxy)-2-(2-pyrimidinyl)-4-pyrimidinyl]benzenesulfonamide. The p-tert-butyl-N-[6-chloro-5-(2-methoxyphenoxy)-2-(2-pyrimidinyl)-4-pyrimidinyl]benzene-sulfonamide is then reacted with a sodium ethylene glycol, prepared by the reaction of ethylene glycol and sodium metal in ethylene glycol solvent, to produce Bosentan as sodium salt. The product formed by this method requires three further crystallizations to provide specification grade Bosentan suitable for formulation.

The '740 patent describes the use of sodium metal for the preparation of sodium ethylene glycolate. Sodium metal is an explosive and hazardous reagent and vigorously reacts with water. The use of sodium metal is not advisable for scale up operations. Moreover, the Bosentan obtained by the process described in the '740 patent using sodium metal is not satisfactory from a purity and yield perspective. The overall yield of sulphonamide derivatives by the said process of '740 patent is 53%. Further, the process of '740 patent also leads to formation of unacceptable amounts of impurities along with Bosentan.

Another process for the preparation of Bosentan is reported in U.S. Pat. No. 6,136,971 (hereinafter referred to as the '971 patent) which is multi-step process as illustrated in Path B of Scheme-1. 5-(2-methoxyphenoxy)-2-(2-pyrimidin-2-yl)-4,6 (1H,5H)-pyrimidinedione is reacted with phosphorous oxychloride in toluene to obtain 4,6-dichloro-5-(2-methoxyphenoxy)-2,2'-bipyrimidine, which is further condensed with 4-tert-butylbenzenesulfonamide in the presence of anhydrous potassium carbonate and a phase transfer catalyst (e.g., benzyltriethylammonium chloride) in toluene to obtain p-tert-butyl-N-[6-chloro-5-(2-methoxyphenoxy)-2-(2-pyrimidinyl)-4-pyrimidinyl]benzene sulfonamide potassium salt. The p-tert-butyl-N-[6-chloro-5-(2-methoxyphenoxy)-2-(2-pyrimidinyl)-4-pyrimidinyl]benzenesulfonamide potassium salt is then reacted with ethylene glycol mono-tert-butyl ether in toluene in the presence of granular sodium hydroxide to produce p-tert-butyl-N-[6-(2-tert-butyl-ethoxy)-5-(2-methoxyphenoxy)-[2,2'-bipyrimidin]-4-yl]benzenesulfonamide (Bosentan tert-butyl ether). The Bosentan tert-butyl ether obtained is then reacted with formic acid followed by treatment with absolute ethanol to obtain Bosentan formate monoethanolate. The Bosentan formate monoethanolate is further treated with sodium hydroxide in absolute ethanol and water followed by acidic hydrolysis by treating with hydrochloric acid and then the resulting precipitate is suction-filtered; washed with ethanol-water mixture (1:1) to give crude Bosentan. The crude Bosentan obtained is then purified with mixture of ethanol and water and the resulting precipitate is suction-filtered to give pure Bosentan.

Scheme-I

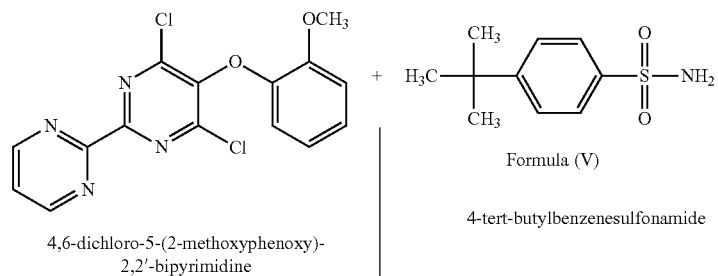

4,6-dichloro-5-(2-methoxyphenoxy)-2,2'-bipyrimidine

Formula (V)

4-tert-butylbenzenesulfonamide

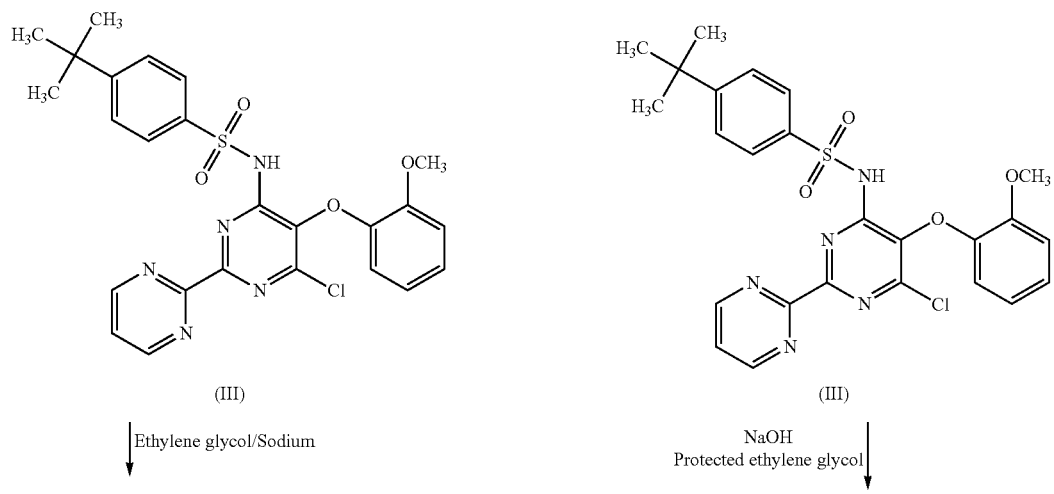

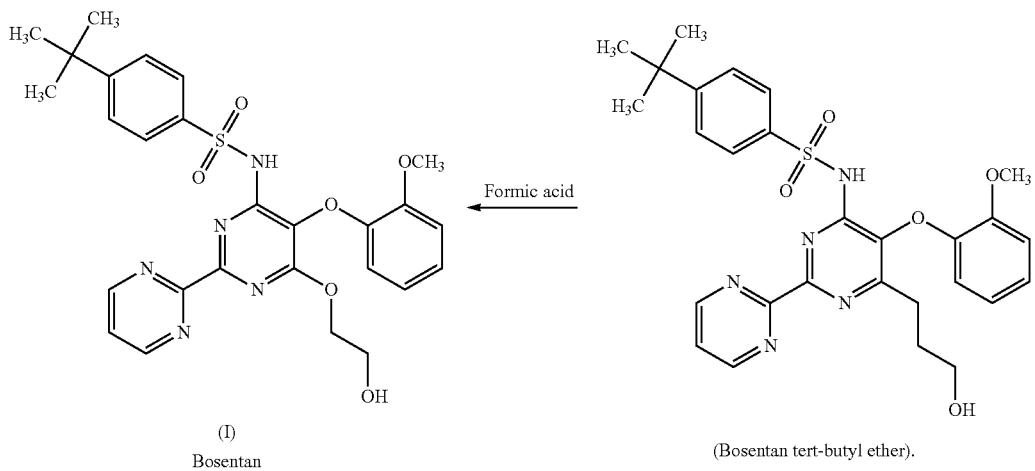

(I) Bosentan    ←Formic acid    (Bosentan tert-butyl ether).

Subsequently few more processes reported in WO 2009/095933A2, WO 2009/112954 A2, WO 2009/093739A1 and WO 2010/032261A1 also follow the reaction sequence represented in Path A of Scheme-1 using multi step processes.

Thus the processes reported in the prior art has following disadvantages:
i) Use of sodium metal which is difficult and not advisable to handle for scale-up operations;
ii) Use of multi-step synthesis where in intermediate are isolated by means of either filtration or centrifugation and subsequent drying of the obtained intermediates before using the same in the next step. The isolation and drying is a very critical step in the production which exposes the production executives to different solvent vapours and also to the isolated solids while handling. The time required to produce a batch is substantially increased as the number of isolations are increased during the production scale and thus multi-step reactions involving multiple filtrations, drying are not suitable for the production;
iii) The processes described in the art does not have satisfactory purity and unacceptable amounts of impurities are generally formed along with product and
iv) Use of ethylene glycol as a solvent along with sodium metal causes formation of high concentration of dimer impurity of formula (VI) which is very difficult to remove from the Bosentan.

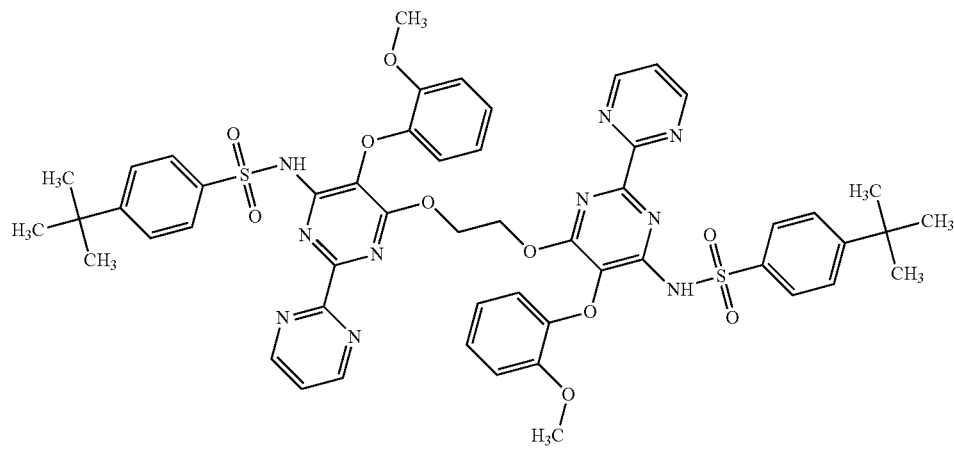

Dimer Impurity Formula (VI)

v) The prior art processes use strong base and high temperature which leads to generation of 6-hydroxy impurity of formula (VII) at higher concentration.

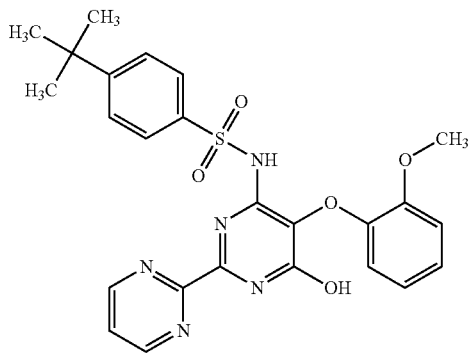

6-hydroxy impurity of formula (VII)

Hence, there remains a need for providing efficient, industrially feasible and economically viable process for the manufacture of Bosentan to substantially eliminate the problems associated with the prior art, and that will be suitable for large-scale preparation such that the process will be safe to handle, simple and easy to carry out, high yield and purity of the product.

SUMMARY

An aspect of the invention is to provide novel ammonium salt of Bosentan of the formula (VIII); which is substantially free from dimer impurity of formula (VI) and 6-hydroxy impurity of formula (VII).

Another aspect of the invention is to provide novel ammonium salt of Bosentan of the formula (VIII); which is either in crystalline form or amorphous form.

Another aspect of the invention is to provide a single pot process for the preparation of novel ammonium salt of Bosentan of the formula (VIII); wherein the process being carried out is a single pot process that eliminates isolation of the intermediate by centrifugation and drying of the intermediate in the production, thus substantially reduces the turnaround time of the batch and also avoids the exposure of the production worker to the solvent vapors and solid handling thereby making the process safe to handle, economical; simple and easy to carry out.

Another aspect of the invention is to provide a single pot process for the preparation of novel ammonium salt of Bosentan of the formula (VIII); wherein the entire process is carried out in a single pot in the presence of base and solvent; thereby making the process simple and easy to carry out.

Yet another aspect of the invention is to provide a single pot process for the preparations of novel ammonium salt of Bosentan of the formula (VIII), wherein consumption of solvent and reagent is substantially reduced which results in reduction of the generation of effluent thereby making the process eco-friendly.

Yet another aspect of the invention is to provide a single pot process for the preparations of novel ammonium salt of Bosentan of the formula (VIII); wherein isolation of ammonium salt of formula (VIII) reduces the formation of dimer impurity of formula (VI) and 6-hydroxy impurity of formula (VII) and thus reduces the load on purification process thereby making the process efficient, simple, easy to carry out, economical and safe to handle.

Yet another aspect of the invention is to provide a process for the preparations of crystalline form of ammonium salt of Bosentan of formula (VIII).

Yet another aspect of the invention is to provide a process for the preparations of amorphous form of ammonium salt of Bosentan of formula (VIII).

Yet another aspect of the invention is to provide Bosentan of the formula (I) which is substantially free from dimer impurity of formula (VI) and 6-hydroxy impurity of formula (VII).

Yet another aspect of the invention is to provide a novel process for the preparation of Bosentan of formula (I) wherein the ammonium salt of Bosentan of the formula (VIII) is converted into Bosentan of formula (I) on hydrolysis wherein the process is simple and easy to carry out.

Yet another object of the invention is to provide the purification process for Bosentan of formula (I); which substantially reduces the impurities generated in the process without losing the yield; thus making the process economic.

Yet another aspect of the invention is to provide crystalline Bosentan Monohydrate of the formula (II) which is substantially free from dimer impurity of formula (VI) and 6-hydroxy impurity of formula (VII).

Yet another aspect of the invention is to provide a process for the preparation of Bosentan Monohydrate of formula (II) wherein monohydrate of formula (VII) is substantially free from dimer impurity of formula (VI) and 6-hydroxy impurity of formula (VII).

FIG. 1: X-ray powder diffraction ('XRD') pattern of crystalline form of ammonium salt of Bosentan of the formula (VIII).

Figure 2:
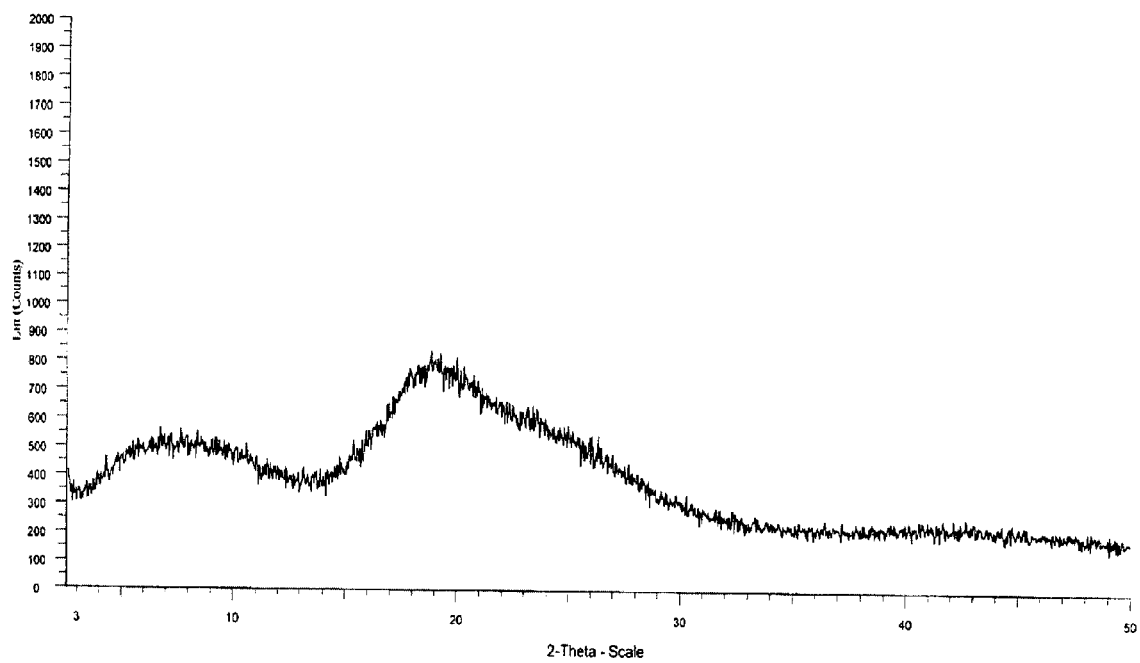

FIG. 2: X-ray powder diffraction ('XRD') pattern of amorphous form of ammonium salt of Bosentan of the formula (VIII).

Figure 3:
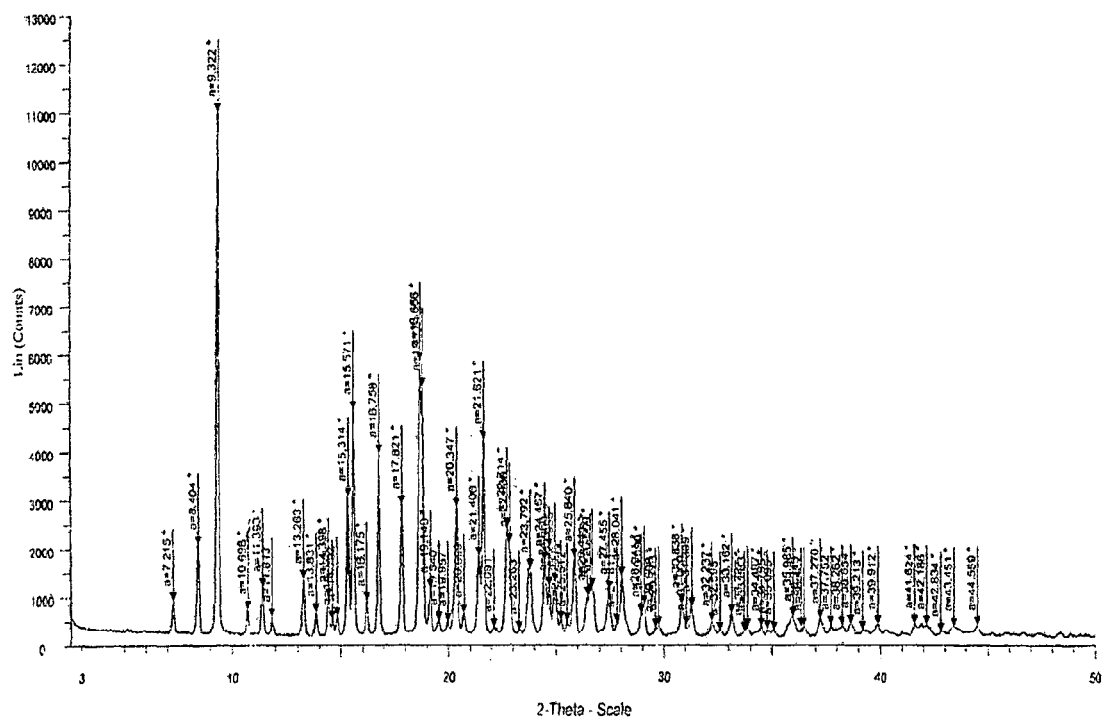

FIG. 3: X-ray powder diffraction ('XRD') pattern of crystalline form of Bosentan Monohydrate of the formula (II).

Figure 4:
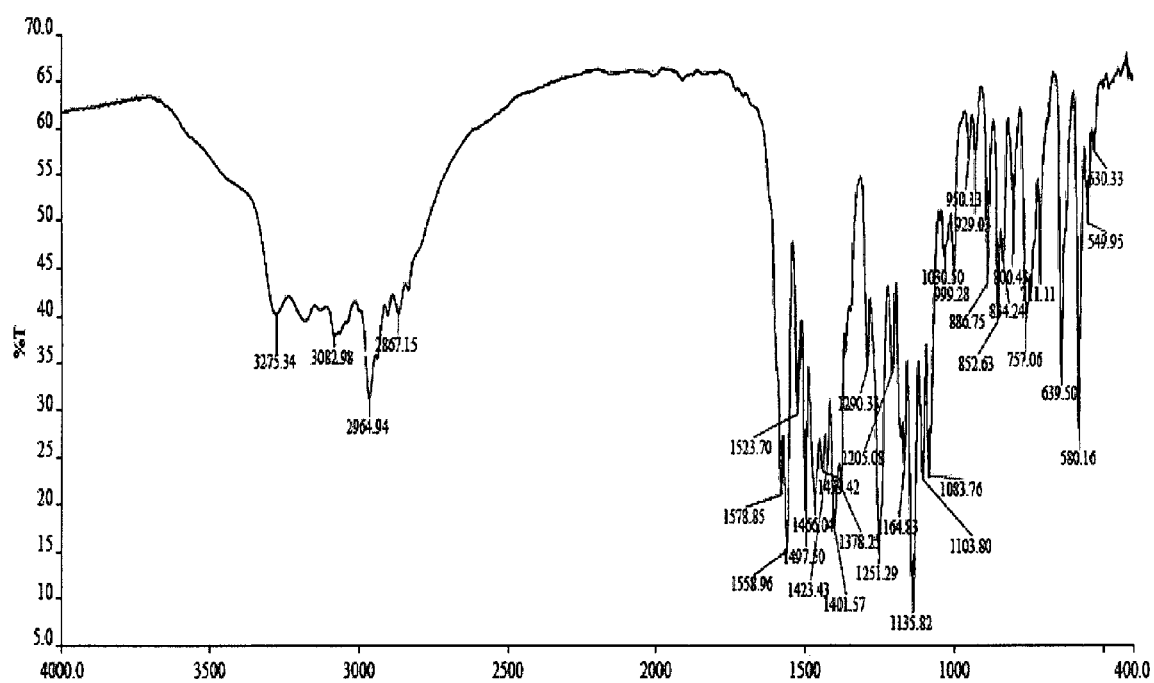

FIG. 4: IR spectrum of ammonium salt of Bosentan of the formula (VIII).

Figure 5:
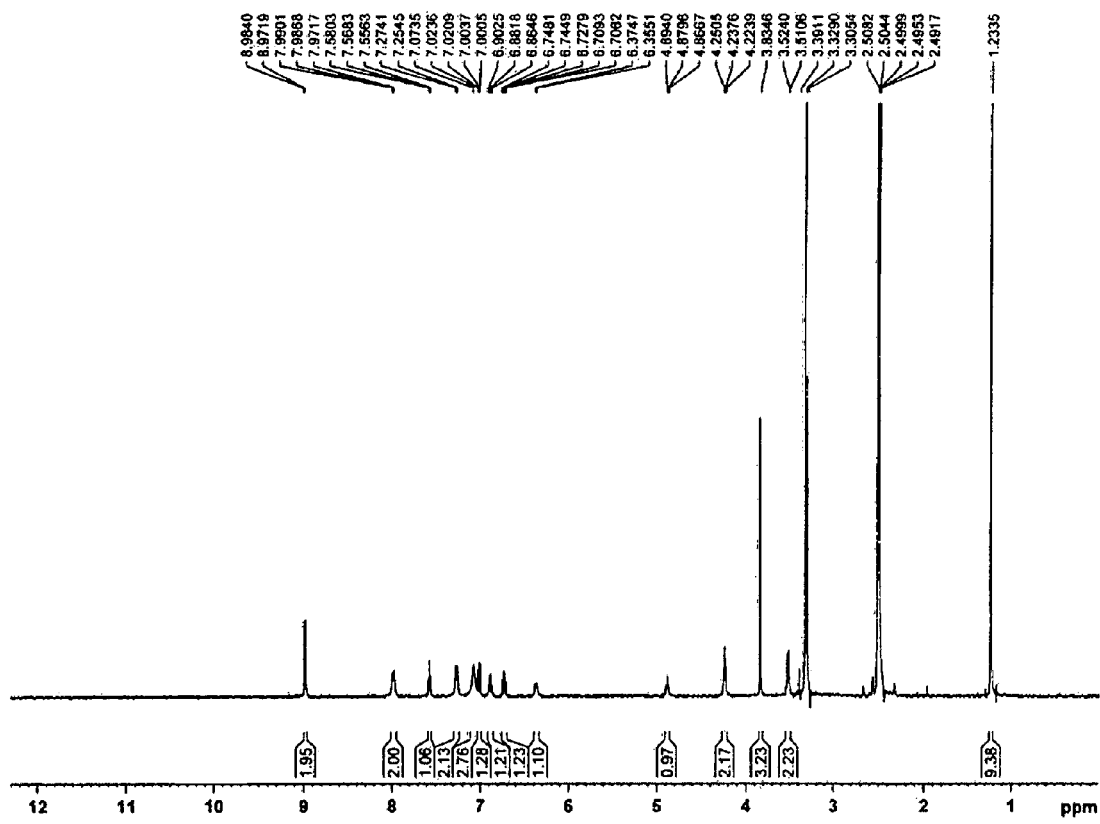

FIG. 5: NMR spectrum of ammonium salt of Bosentan of the formula (VIII).

Figure 6:
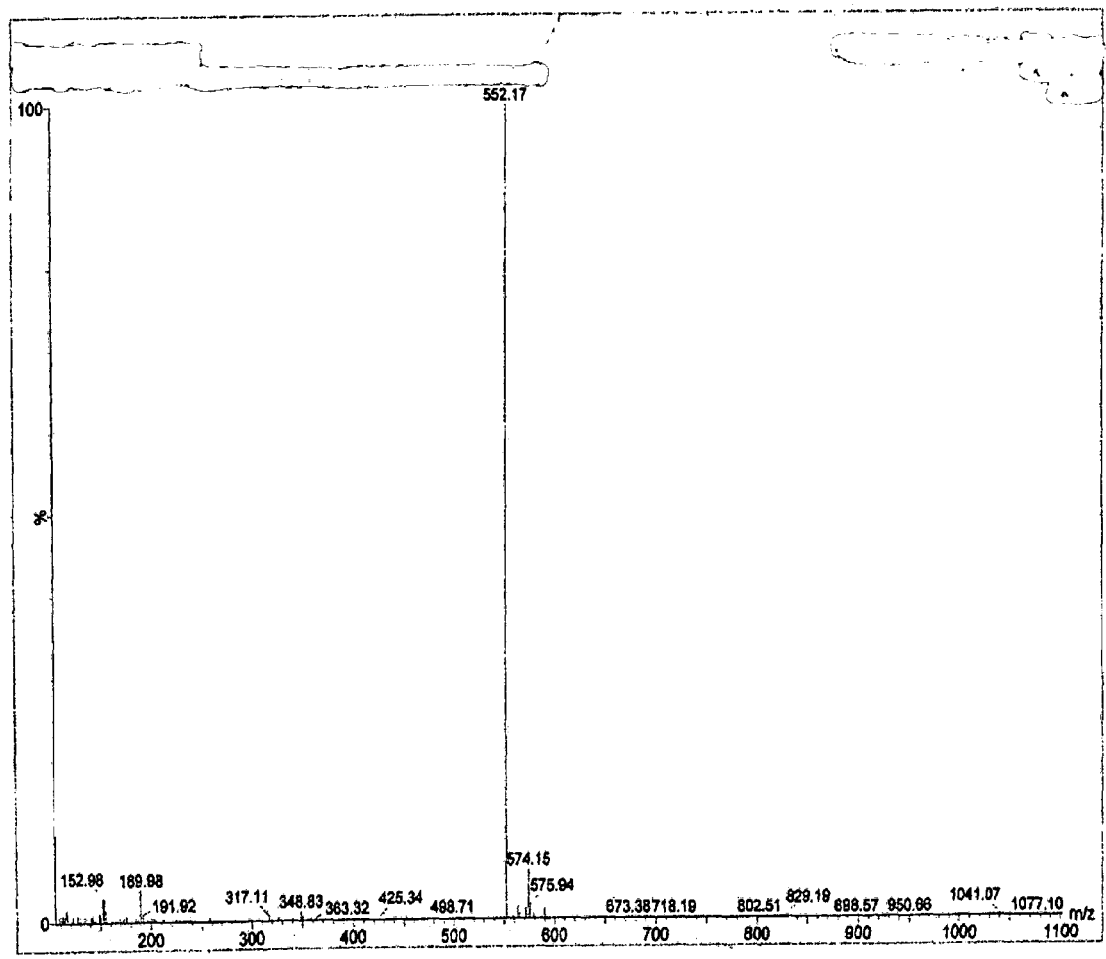

FIG. 6: Mass Spectrum of Bosentan Monohydrate of the formula (II).

DETAILED DESCRIPTION

According to one of the embodiment of the invention, there is provided a novel ammonium salt of Bosentan of formula (VIII);

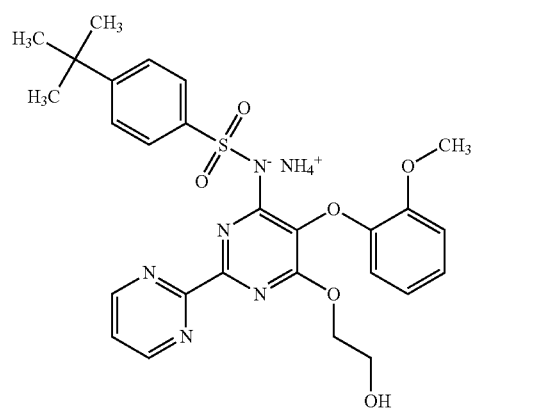

Formula (VIII)

characterized by melting point, IR Spectrum, NMR and elemental analysis.

The melting point of ammonium salt of Bosentan of the formula (VIII) is 172-174° C.

The IR spectrum of ammonium salt of Bosentan of the formula (VIII) has characteristic peaks at 580, 1136, 1251, 1558, 2965, 3277 cm$^{-1}$.

The NMR, $^1$H NMR (DMSO) of ammonium salt of Bosentan of the formula (VIII) having characteristic peaks at δ 8.97-8.98 (d, 2H), 7.97-7.99 (d, 2H), 7.55-7.58 (t, 1H), 7.25-7.27 (d, 2H), 7.00-7.02 (d, 1H) 6.86-6.90) (t, 1H) 6.70-6.74 (t, 1H) 6.35-6.37 (d, 1H) 4.86-4.89 (t, 1H), 4.22-4.25 (t, 2H) 3.83 (s, 3H) 3.51-3.52 (q, 2H) 1.23 (s, 9H) as demonstrated in FIG. 5.

The elemental analysis for $C_{27}H_{32}N_6O_6S$ shows as C, 56.98(%); H, 5.10(%); N, 14.77(%) and found as C, 56.67 (%); H, 5.50(%); N, 14.78(%).

According to another embodiment of the invention, there is provided a novel crystalline form of ammonium salt of Bosentan of formula (VIII); characterized by XRD. All of Bosentan of formula (VIII); characterized by PXRD. PXRD spectrum of amorphous form of ammonium salt of Bosentan of formula (VIII) is shown in figure (II).

According to the invention, there is provided a novel single pot process for the preparations of ammonium salt of Bosentan of the formula (VIII) comprises:

reacting the 4,6-dichloro-5-(2-methoxyphenoxy)-2,2'-bipyrimidine of formula (III) with 4-tert-butylbenzenesulfonamide of formula (IV) in the presence of solvent and a base; adding ethylene glycol of the formula (V) to the reaction mass, continuing the reaction till its completion; and isolating the ammonium salt of Bosentan of the formula (VIII) as presented in Scheme-2.

Scheme-2: Schematic representation for the preparation of ammonium salt of Bosentan of Formula (VIII)

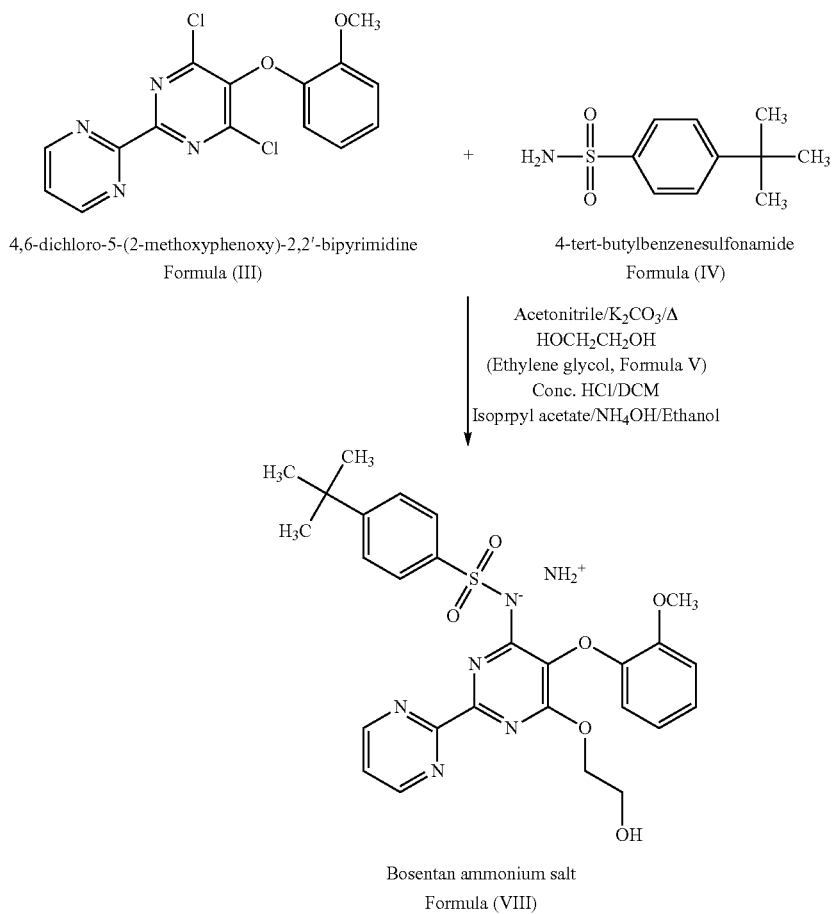

PXRD data reported herein obtained using Cu k alpha radiation, having the wavelength 1.541 A°, and were obtained using Bruker Axe D8 Advance Powder X-ray Diffractometer. XRD spectrum of ammonium salt of Bosentan of formula (VIII) is shown in figure (I). The novel crystalline form of ammonium salt of Bosentan is characterized by its XPRD pattern having characteristic peaks at 5.96, 6.79, 9.09, 9.26, 10.52, 16.64, 17.60, 18.14, 18.53, 22.49, 24.29, 24.91, and 27.5±0.2 degrees 2θ.

According to yet another embodiment of the invention, there is provided a novel amorphous form of ammonium salt The 4,6-dichloro-5-(2-methoxyphenoxy)-2,2'-bipyrimidine of formula (III) is reacted with 4-tert-butylbenzenesulfonamide of formula (IV) in the presence of a polar aprotic solvent and a base at temperature in the range of 30-150° C. This reaction is carried out at the temperature range of 50° C. to 150° C.; preferably, 80° C. to 90° C. The reaction completion is monitored by HPLC or TLC.

The polar aprotic solvent used in the reaction of the formula (III) and formula (IV) include but not limited to $C_3$-$C_6$ Ketones such as acetone, methyl isobutyl ketone, ethyl methyl ketone and the like; nitriles such as acetonitrile and the like; $C_3$-$C_6$ amides such as dimethyl formamide, dimethyl acetamide, N-methyl-2-pyrrolidone, hexamethyl phsopharamide, and the like; $C_2$-$C_8$ ethers and cyclic ether, substituted cyclic ethers, such as diethyl ether, isopropyl ether, methyl tertiary butyl ether, tetrahydrofuran, 1,4-dioxan, 2-methyl tetrahydrofuran and the like; dimethylsulfoxide or combinations thereof. Preferably, the polar aprotic solvent used are selected from acetonitrile, dimethyl formamide, dimethyl sulphoxide or combinations thereof; more preferably acetonitrile.

The base used in the reaction of the formula (III) and formula (IV) is selected from organic or inorganic, which includes but not limited to sodium carbonate, potassium carbonate, sodium bicarbonate, potassium bicarbonate, cesium carbonate, calcium carbonate, sodium hydroxide, potassium hydroxide, cesium hydroxide, barium hydroxide, lithium hydroxide and the like or mixture thereof. Preferably the base used are selected from potassium carbonate, sodium carbonate, cesium carbonate or calcium carbonate; more preferably potassium carbonate.

To the reaction mass, ethylene glycol of formula (V) was added; and the temperature of the reaction mass is maintained between 50° C.-150° C., preferably 80° C. to 90° C. till the completion of reaction. The completion of the reaction is monitored by HPLC or TLC Optionally, the reaction mass is cooled to 20° C.-25° C. before starting the addition of ethylene glycol; subsequently the temperature of the reaction mass is increased to about 50° C.-150° C., preferably 80° C. to 90° C. till the completion of reaction. The completion of the reaction is monitored by HPLC or TLC A term herein "completion" means attaining the content of the starting material to a desired or a specified limits.

The reaction mass obtained is optionally filtered to remove the inorganic salts and the filtrate obtained is used in the preparation of ammonium salt of Bosentan of the formula (VIII). The filtration is carried out in hot condition to avoid precipitation.

Isolation of the ammonium salt of Bosentan of the formula (VIII) is carried out by
  a. cooling the reaction mass followed by addition of water and adjusting the pH of the reaction mass to pH 1 to 4 and extracting the aqueous reaction mass by suitable organic solvent followed by concentrating the organic layer to obtain residue; and
  b. adding solvent and ammonia or ammonium hydroxide to the residue of step (a) and heating the obtained mixture till clear solution is obtained, followed by cooling the reaction mass and filtering the ammonium salt of Bosentan of the formula (VIII).

The reaction mass of step (a) is cooled to 20° C. to 40° C., preferably to 25° C. to 30° C. Preferably, the pH of the reaction mass of step (a) is adjusted to pH 1 to 4, preferably between 1 to 2. The acid used in step (a) to adjust the pH of the reaction mass may include but not limited to tartaric acid, oxalic acid, mandelic acid, fumaric acid, acetic acid, formic acid and the like or from inorganic acids such as hydrochloric acid, nitric acid, sulfuric acid, hydrobromic acid, para-toluene sulfonic acid and the like and mixtures thereof.

The solvent used in step (a) for the extraction includes but not limited to aliphatic chlorinated hydrocarbons such as dichloromethane, dichloroethane and the like; hydrocarbons such as toluene, xylene, cyclohexanes, hexanes, heptanes, and the like; $C_2$-$C_6$ alkyl acetates such as ethyl acetate, isopropyl acetate, butyl acetate, and the like; $C_2$-$C_8$ ethers such as diethyl ether, isopropyl ether, methyl tertiary butyl ether and the like. Particularly, the solvent used is aliphatic chlorinated hydrocarbons such as dichloromethane, dichloroethane and the like; more particularly, the solvent used is dichloromethane.

The organic layer separated in step (a) is optionally washed by brine solution and is dried over sodium sulfate. In step (a), the dried organic layer is subjected to distillation under reduced pressure to obtain residue.

In step (b), the solvent used to dissolve the residue is selected from $C_3$-$C_6$ Ketones such as acetone, ethyl methyl ketone, methyl isobutyl ketone and the like; aromatic hydrocarbons such as toluene, xylenes, and the like; dimethyl sulfoxide; dimethyl formamide; $C_1$-$C_5$ alkyl alcohol such as methanol, ethanol, propanol, iso-propanol, n-butanol, tert-butanol, n-pentanol and the like; acetonitrile; $C_2$-$C_6$ alkyl acetates such as ethyl acetate, isopropyl acetate, butyl acetate, and the like; $C_2$-$C_8$ ethers such as diethyl ether, isopropyl ether, methyl tertiary butyl ether and the like; tetrahydrofuran, water, and base such as ammonia, ammonium hydroxide, ammonium acetate, ammonium carbonate, or combination thereof, preferably mixtures of alkyl acetate such as ethyl acetate, isopropyl acetate, butyl acetate, and the like, alcohol such as methanol, ethanol, propanol, iso-propanol, n-butanol, tert-butanol, n-pentanol and the like and aqueous ammonia, more preferably the mixture of isopropyl acetate, ethanol and aqueous ammonia.

The solution/or suspension obtained in step (b) after dissolving the residue is optionally heated to the temperature between 40° C. to near reflux temperature of the solvent, preferably at 50° C. to 60° C.

A term herein "reflux temperature" means the temperature at which the solvent or the solvent system refluxes or boils at atmospheric pressure In step (b), the solution is maintained at 50° C. to 60° C. over a period of 10 to 120 minutes, preferably 25 to 30 minutes prior to cooling.

In step (b), the solution obtained is cooled to temperature between 0° C. and 45° C.; preferably 0° C. to 20° C.; more preferably between 0° C. to 10° C. to precipitate the ammonium salt of Bosentan of the formula (VIII) followed by isolating the ammonium salt by filtration. The obtained solid is optionally washed by pre-chilled methanol.

The ammonium salt of Bosentan of formula (VIII) is optionally purifying using appropriate solvent.

The ammonium salt of Bosentan of the formula (VIII) is dried under reduced pressure until the residual solvent content reduces within the limits as per the International Conference on Harmonization of Technical Requirements for Registration of Pharmaceuticals for Human Use (ICH) guidelines.

The ammonium salt of Bosentan of formula (VIII) is dried either at atmospheric pressure or reduced pressures and at a temperature in the range of 35° C. to 70° C. Temperatures and pressures are chosen based on the volatility of the solvent being used, and the foregoing should be considered as only a general guidance.

The solvent used in the purification of ammonium salt of Bosentan of the formula (VIII) is mixture of isopropyl acetate, ethanol and aqueous ammonia.

Ammonium salt of Bosentan of the formula (VIII) prepared according to the invention have 0.05% of dimer impurity of formula (VI) and 0.40% 6-hydroxy impurity of formula (VII). The purity and yield of ammonium salt of Bosentan of the formula (VIII) are 99.40% and 86.0% respectively.

Isolation of the ammonium salt of Bosentan of the formula (VIII) according to the invention provides crystalline form of ammonium salt of Bosentan.

Crystalline form of ammonium salt of Bosentan of the formula (VIII) prepared according to the invention has 0.05% of dimer impurity of formula (VI) and 0.4% 6-hydroxy impurity of formula (VII). The purity and yield of crystalline form of ammonium salt of Bosentan of the formula (VIII) are 99.40% and 86.0% respectively.

According to yet another embodiment of the invention, there is provided a process for the preparation of amorphous form of ammonium salt of Bosentan, said process comprising: a) providing solution of crystalline or mixture of crystalline and amorphous form of ammonium salt of Bosentan in solvent; b) removing the solvent to form a solid residue; and c) isolating the solid residue to obtain the amorphous form of ammonium salt of Bosentan.

The solution of crystalline or mixture of crystalline and amorphous form of ammonium salt of Bosentan may be obtained by dissolving crystalline ammonium salt of Bosentan in a suitable solvent. The solvents include but not limited to alcohols like methanol, ethanol, iso-propanol, and the like; halogenated hydrocarbons like dichloromethane, 1,2-dichloroethane, chloroform, carbon tetrachloride and the like; ketones like acetone, ethyl methyl ketone, methyl isobutyl ketone and the like; esters like ethyl acetate, n-propyl acetate, n-butyl acetate, t-butyl acetate and the like; ethers like diethyl ether, dimethyl ether, di-isopropyl ether and the like; hydrocarbons such as toluene, xylene, n-heptane, cyclohexane, n-hexane and the like; nitriles such as acetonitriles, propionitrile and the like; or mixtures thereof.

The removal of the solvent from the solution of ammonium salt of Bosentan may be affected at an increased temperature, preferably at reflux temperature, and/or reduced pressure. The removal of solvent is carried out by filtration, distillation, evaporation, atmospheric distillation, distillation under vacuum, lyophilization, Freeze drying, spray drying, agitated thin film drying (ATFD), etc.

The solid residue obtained after solvent removal may be isolated and dried using conventional methods. The advantages of the process include simplicity, eco-friendliness and suitability for commercial use. The amorphous form of ammonium salt of Bosentan prepared according to the invention is characterized by PXRD, which is shown in FIG. 2.

Amorphous form of ammonium salt of Bosentan of the formula (VIII) prepared according to the invention has 0.05% of dimer impurity of formula (VI) and 0.40% 6-hydroxy impurity of formula (VII). The purity and yield of amorphous form of ammonium salt of Bosentan of the formula (VIII) are 99.50% and 85.0% respectively.

According to the invention, there is provided a process for the preparation of Bosentan of the formula (I); the process comprises hydrolyzing the ammonium salt of Bosentan of the formula (VIII) by adding water to ammonium salt, treating it with acid and isolating Bosentan of the formula (I).

Isolation of Bosentan of the formula (I) is carried out by extracting the Bosentan of the formula (I) from hydrolyzed reaction mass using a solvent and concentrating the organic solvent to obtain Bosentan of formula (I) as a residue.

Preferably, the hydrolysis of the ammonium salt of Bosentan of the formula (VIII) is carried out by dissolving it in water followed by adjusting the pH of the reaction mass to pH 1 to 6; preferably pH around 4 to obtain Bosentan of the formula (I). This acidified/hydrolyzed reaction mass containing Bosentan of the formula (I) which is extracted using solvent. The solvent used in extraction of Bosentan of the formula (I) includes but not limited to hydrocarbon or halogenated hydrocarbon such as dichloromethane, dichloroethane, chloroform and the like; $C_2$-$C_6$ alkyl acetates such as ethylacetate, isopropyl acetate, butyl acetate, and the like; $C_2$-$C_8$ ethers such as diethyl ether, isopropyl ether, methyl tertiary butyl ether and the like; hydrocarbons such as toluene, xylene, cyclohexanes, hexanes, heptanes, and the like. Preferably, the solvent used for the extraction of Bosentan of the formula (I) is dichloromethane. The organic layer containing pure Bosentan is distilled off under reduced pressure to obtain Bosentan as residue. The organic layer may be washed with water, followed by washing with brine solution, and dried optionally over sodium sulfate before subjecting it to distillation.

The obtained wet Bosentan of the formula (I) is purified by treating it with a solvent and subsequently heating the mixture to reflux temperature followed by gradually cooling the mixture to 0° C. to 50° C.; maintaining the mixture at same temperature for 30 to 60 minutes and filtering the pure product.

The solvent used for the purification of Bosentan of the formula (I) includes but not limited to nitriles such as acetonitrile; alcohols such as ethanol, methanol, propanol and the like; water or mixtures thereof. Preferably, the solvent used for the purification of Bosentan of the formula (I) is mixture of acetonitrile and methanol.

Bosentan of the formula (I) prepared according to the invention has around 0.02% of dimer impurity of formula (VI) and around 0.03% of 6-hydroxy impurity of formula (VII). The purity and yield of Bosentan of the formula (I) are around 99.85% and around 70.0% (calculated from compound of Formula (III)) respectively.

According to the invention, there is also provided a process for the preparation of Bosentan monohydrate of the formula (II); the process comprises dissolving the Bosentan of the formula (I) in solvent, heating the mixture to get a clear solution, adding the activated charcoal as decolorizing agent to the resulting solution, continuing the heating followed by removing the charcoal by filtration, adding water to the hot solution, cooling the solution to 20° C.-30° C. to precipitate the pure Bosentan monohydrate of the formula (II) and filtering the highly pure Bosentan monohydrate of the formula (II).

The solvent used in the preparation of the Bosentan of the formula (I) is dissolved in alcohol such as methanol, ethanol, propanol, butanol, etc; preferably ethanol.

The highly pure Bosentan Monohydrate is subjected to drying at 35° C. to 40° C. till achieving the desired moisture content.

According to the invention, there is provided Bosentan monohydrate of the formula (II) which has around 0.01% dimer impurity of formula (VI) and around 0.02% of 6-hydroxy impurity of formula (VII) respectively as represented in Scheme-3. The purity and yield of Bosentan monohydrate of the formula (II) are around 99.90% and 68.7% (Calculated form compound of Formula (III)) respectively.

XRD spectrum of Bosentan monohydrate of formula (II) is shown in figure (II). The novel crystalline form of Bosentan monohydrate is characterized by its XPRD pattern having characteristic peaks at 7.2, 10.69, 13.26, 15.57, 19.14, 19.95, 21.62±0.2 degrees 2θ.

The term 'highly pure Bosentan or highly pure Bosentan monohydrate' as used herein refers to the highly pure Bosentan or highly pure Bosentan monohydrate having total purity of greater than 99%, specifically greater than 99.5%, more specifically greater than 99.8% and most specifically about 99.9% (measured by HPLC)

Scheme-3: Schematic representation for the preparation of Bosentan monohydrate of Formula (II)

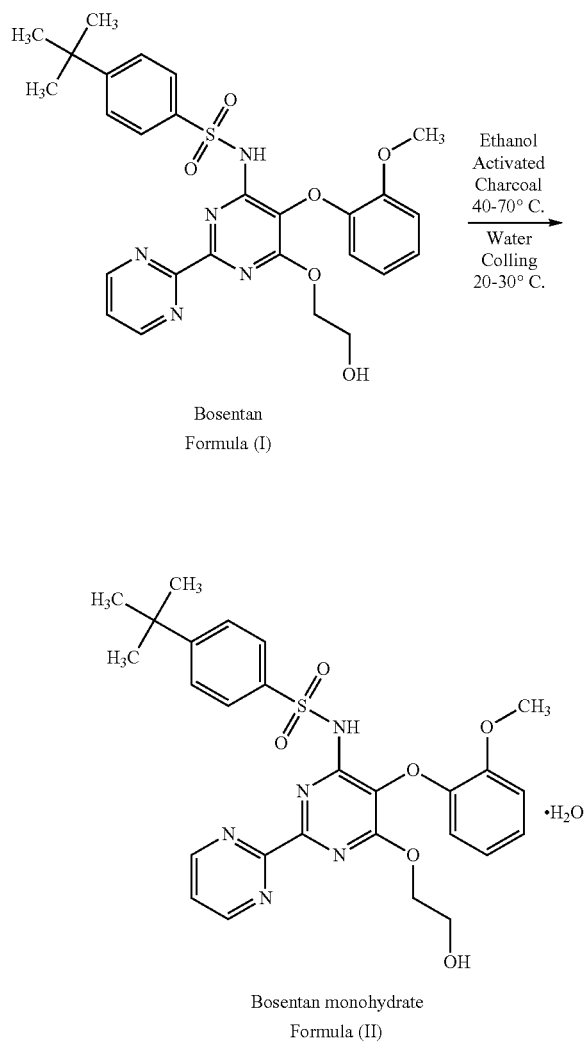

The isolation of crystalline ammonium salt of Bosentan of formula (VIII) and purification of Bosentan removes the impurities, namely dimer impurity of formula (VI) and 6-hydroxy impurity of formula (VII) which are generated during the production of Bosentan.

Thus process for the manufacture of ammonium salt of Bosentan of formula (VIII) of the invention is a single pot process. The present invention eliminates centrifuging of the intermediate, isolation of the intermediate and drying of the intermediate; thus substantially reducing the reaction time and also avoiding the exposure of the production executive to the solvents and solid handling thereby making the process safe to handle, economical, simple and easy to carry out. The entire process is carried out in a single step in the presence of base and solvent; thereby making the process simple and easy to carry out. The consumption of solvent and reagent is substantially reduced which results in reduction of the generation of effluent thereby making the process eco-friendly. The process substantially eliminates dimer impurity of Formula (VI) and 6-hydroxy impurity of Formula (VII) and thus reduces the load on purification process thereby making the process simple, easy to carry out, economical and safe to handle.

The following experimental examples are illustrative of the invention but not limitative of the scope thereof:

Example 1

Preparation of Ammonium Salt of Bosentan

To a stirred solution of 4,6 dichloro-5-(2-methoxybenzyl)-2,2-bipyrimidine (100 gm) in acetonitrile (1000 ml), 4-tert-butylbenzenesulphonamide (67.16 gm) and potassium carbonate (340 gm) were added with stirring at 25° C. to 30° C. The reaction mass was stirred at 80° C. to 85° C. for 2 to 4 hours. After completion of the reaction which was monitored by TLC, ethylene glycol (1000 ml) was added to the reaction mass and the resulting reaction mixture was further stirred at 80° C. to 85° C. for 25 to 30 hours. After completion of the reaction (by HPLC), the reaction solution was cooled at 25° C. to 30° C. and it was diluted with water (1000 ml). The pH of the solution was adjusted to pH 4.0 to 5.0 using concentrated hydrochloric acid.

The resulting reaction solution was extracted with dichloromethane (1000 ml). The dichloromethane layer was washed with 5% brine solution (2×1000 ml) and distilled off completely to obtain the residue. The residue was suspended with 3:1 mixture of isopropyl acetate (780 ml), ethanol (260 ml) followed by ammonium hydroxide (158 ml) and the resulting mixture was heated at 50° C. to 55° C. for 30 minutes. The mixture was cooled to 5° C.-10° C. and it was maintained for 5 to 6 hours. The solid obtained was filtered and dried to obtain the ammonium salt of Bosentan 145.0 gm [86.4%]. The salt is characterized by melting point, IR, NMR and elemental analysis. Melting Point: 172-174° C.;

IR having characteristic peaks at 580, 1136, 1251, 1558, 2965, 3277 $cm^{-1}$;

The NMR, $^1H$ NMR (DMSO) of ammonium salt of Bosentan of the formula (VIII) having characteristic peaks at δ 8.97-8.98 (d, 2H), 7.97-7.99 (d, 2H), 7.55-7.58 (t, 1H), 7.25-7.27 (d, 2H), 7.00-7.02 (d, 1H) 6.86-6.90) (t, 1H) 6.70-6.74 (t, 1H) 6.35-6.37 (d, 1H) 4.86-4.89 (t, 1H), 4.22-4.25 (t, 2H) 3.83 (s, 3H) 3.51-3.52 (q, 2H) 1.23 (s, 9H) as demonstrated in FIG. 5.

Elemental analysis for $C_{27}H_{32}N_6O_6S$: Theoretical (%) C, 56.98; H, 5.10; N, 14.77.

Found (%) C, 56.67; H, 5.50; N, 14.78.

The novel crystalline form of ammonium salt of Bosentan is characterized by its XPRD pattern having characteristic peaks at 5.96, 6.79, 9.09, 9.26, 10.52, 16.64, 17.60, 18.14, 18.53, 22.49, 24.29, 24.91, and 27.5±0.2 degrees 2θ and its XRPD pattern is as per FIG. 1

Example 2

Preparation of Novel Amorphous Ammonium Salt of Bosentan 100 grams of crystalline ammonium salt of bosentan was dissolved in 500 ml of dichloromethane and stirred for 15-20 minutes to get a clear solution at temperature 35° C. to 40° C. The solvent was removed under reduced pressure at temperature 35° C. to 40° C. The obtained mass was degassed for 30 minutes and the amorphous ammonium salt of Bosentan obtained was analyzed for its XRD which are illustrated in FIG. 2.

Example 3

Preparation of Bosentan Monohydrate

To a stirred solution of 4,6 dichloro-5-(2-methoxybenzyl)-2,2-bipyrimidine (2.0 kg) in acetonitrile (20.0 lit), 4-tertbutylbenzenesulphonamide (1.34 kg) and potassium carbonate (6.8 kg) were added with stirring at 25° C. to 30° C. The reaction mass was stirred at 80° C. to 85° C. till completion of the reaction (monitored by TLC). To this reaction mass, ethylene glycol (20.0 lit) was added and continued heating at 80° C. to 85° C. till completion of the reaction (monitored by HPLC). After ensuring the completion, the reaction solution was cooled at 25° C. to 30° C. It was diluted with water (20.0 lit) and the pH of the solution was adjusted to 3 to 4 using concentrated hydrochloric acid.

The resulting reaction solution was extracted with dichloromethane (20.0 lit). The dichloromethane layer was washed with 5% brine solution (2×20.0 lit) and the layer was concentrated to obtain the residue. The residue was dissolved in the mixture of isopropyl acetate (16.0 lit) and ethanol (5.3 lit) and then treated with ammonium hydroxide (3.2 lit). The mixture was heated at 50° C. to 55° C. for 30 min followed by cooling the mixture to 5° C. to 10° C. and it was maintained for 6 to 8 hours. The mixture was filtered to get west solid of Bosentan ammonium salt. The wet solid obtained is suspended in mixture of dichloromethane (10.0 lit) and water (10.0 lit) and the pH of the mixture was adjusted to 1 to 4 using conc. hydrochloric acid. The dichloromethane layer was separated and was washed with water (10.0 lit). The layer was subjected to distillation to remove dichloromethane completely to obtain the Bosentan residue. The residue was further dissolved in acetonitrile (3.0 lit) and methanol (16.0 lit) at 50° C. to 55° C. and the solution was cooled to 5° C. to 10° C. and was maintained at same temperature for 1 to 2 hours. The solid obtained was filtered to furnish the pure Bosentan.

The wet Bosentan was dissolved in ethanol (4.4 lit) at 50° C. to 55° C. and decolorized with activated charcoal. The solution was heated at 50° C. to 55° C. To this solution, water (4.4 lit) was added and was stirred for 20 min. The solution was cooled to 25° C. to 30° C. and was maintained at same temperature for 60 min. The crystalline solid obtained was filtered, washed with chilled ethanol, and dried under vacuum (650-700 mm/Hg) at 35° C. to 40° C. to afford 2.20 kg [68.7% yield] of Bosentan monohydrate as a white crystalline solid.

Purity: 99.9%; Dimer impurity: 0.02%, Hydroxy impurity: 0.03%; HPLC purity: 99.90%.

MS; m/z 552.17 (m$^+$+1) as demonstrated in FIG. 6.

$^1$H NMR (CDCl$_3$) δ 8.98-8.99 (d, 2H), 8.75 (s, 1H), 8.39-8.41 (d, 2H), 7.41 (t, 1H), 7.39-7.40 (d, 2H), 6.84-7.13 (m 4H), 4.89 (s, 1H), 4.58-4.56 (t, 2H), 3.93 (s, 3H), 3.84 (t, 2H), 1.27 (s, 9H),

Example 4

Preparation of Ammonium Salt of Bosentan

To a stirred solution of 4,6-dichloro-5-(2-methoxyphenoxy)-2,2'-bipyrimidine (25 gm) in acetonitrile (250 ml), potassium carbonate (85 gm) and 4-tert-butylbenzenesulfonamide (16.79 gm) were added and the reaction mixture was heated to 80° C. to 85° C. for 5 to 6 hours. After the completion of the reaction, ethylene glycol (187 gm) was added to the reaction mass at 85° C. to 90° C. and maintained the reaction mass at same temperature for 16 to 18 hours. The reaction mass was then cooled to 25° C. to 30° C., and the pH of the reaction mass was adjusted to 2 to 3 by adding tartaric acid solution. The precipitated solid was stirred and filtered. The crude Bosentan was washed with mixture of methanol and water. The crude Bosentan: (35 g).

The crude Bosentan (35 gm) obtained was treated with mixture of isopropyl acetate (105 ml), ethanol (35 ml) and ammonium hydroxide solution (8.75 ml) and the resulting mixture was heated to 55° C. to 60° C. for 30 minutes, followed by cooling reaction mass to 0° C. to 5° C. The reaction mass was maintained for 3 to 4 hours at 0° C. to 5° C. The precipitated solid was filtered and dried. (26 gm).

Yield: 70%;

Purity: 99.5%; dimer impurity of formula (VI): 0.05%; 6-hydroxy impurity of formula (VII): 0.06%.

Example 5

Preparation of Bosentan Monohydrate

To a stirred solution of 4,6-dichloro-5-(2-methoxyphenoxy)-2,2'-bipyrimidine (50 gm) in acetonitrile (500 ml), potassium carbonate (150 gm) and 4-tert-butylbenzenesulfonamide (33.58 gm) were added and the reaction mass was heated to 80° C. to 85° C. for 5 to 6 hours. After completion of the reaction, ethylene glycol (262.5 gm) was added to the reaction mass at 85° C. to 90° C. and the reaction mass was maintained at same temperature for 16 to 18 hours till the reaction completion. The reaction mass was then cooled to 25 to 30° C. and water (500 ml) was added to it. The pH of the reaction mass was adjusted to 2 to 3 using concentrated hydrochloric acid. Dichloromethane (500 ml) was added to the reaction mass and the mixture was stirred for 30 minutes. The dichloromethane layer was separated and it was washed with water (500 ml). The layer was concentrated under reduced pressure to obtain the syrup. Methanol (160 ml) and water (80 ml) were added to the syrup and the mixture was heated to 55° C. to 60° C. for 30 minutes under stirring. The reaction mixture was then cooled to 25° C. to 30° C. for 40 to 45 minutes and the solid obtained was filtered. The solid was washed with methanol (40 ml) to obtain the crude Bosentan (wet weight around 75 gm). To the crude Bosentan (75 gm), isopropyl acetate (225 ml), ethanol (75 ml), and ammonium hydroxide solution (37.2 ml) were added and the mixture was heated to 55° C. to 60° C. for 30 minutes. The reaction mass was then cooled to 0° C. to 5° C. and maintained at 0° C. to 5° C. for 3 to 4 hours. The precipitated pure Bosentan ammonium salt was filtered (yield, 60 gm), washed with chilled isopropylacetate and dried.

To the pure ammonium salt of Bosentan (60 gm), dichloromethane (180 ml) and water (180 ml) were added and the pH of the reaction mixture was adjusted to 5 to 6 using concentrated hydrochloric acid. The reaction mixture was stirred for 30 minutes. The dichloromethane layer was separated and it was washed with water (180 ml). The dichloromethane layer was subjected to evaporation under reduced pressure to obtain syrup. To this syrup, ethanol (120 ml) was added and the mixture was heated to 55° C. to 60° C. to obtain clear solution. Water (120 ml) was slowly added to the clear solution and was stirred for 30 minutes at 55° C. to 60° C. The reaction mixture was cooled to 25° C. to 30° C. and the mixture was stirred for 30 to 45 minutes at 25° C. to 30° C. The solid obtained was filtered and was dried at 40° C. for 2 to 4 hours, to yield Bosentan monohydrate (60 gm).

Yield: 76%;

Purity: 99.8%; dimer impurity of formula (VI): 0.03%; 6-hydroxy impurity of formula (VII): 0.03%; Water content: 3.12% w/w.

Example 6

Preparation of Crystalline Ammonium Salt of Bosentan

To a stirred solution of 4,6-dichloro-5-(2-methoxyphenoxy)-2,2'-bipyrimidine (25 gm) in acetonitrile (375 ml), potassium carbonate (85 gm) and 4-tert-butylbenzenesulfonamide (16.79 gm) were added and the contents were heated to 80° C. to 85° C. for 5 to 6 hours. After the completion of the reaction, ethylene glycol (187 gm) was added at 80° C. to 90° C. and the reaction mass was maintained at same temperature for 16 to 18 hours. The reaction mass was then cooled to 25° C. to 30° C. and it was filtered to remove potassium carbonate. The potassium carbonate residue was washed with acetonitrile (25 ml) and washings are mixed with the main filtrate. The pH of the filtrate was adjusted to 2 to 3 with tartaric acid solution and dichloromethane (250 ml) was added to it and stirred. The organic layer was separated and it was washed with water (250 ml). The layer was concentrated to yield syrup.

To this syrup, methanol (80 ml) and water (40 ml) were added and the resulting mixture was heated to 55° C. to 60° C. for 30 minutes under stirring. The reaction mixture was then cooled to 25° C. to 30° C. for 40 to 45 minutes and the solid obtained was filtered. It was washed with methanol, (20 ml) to obtain crude Bosentan (38 gm) in wet form. To this crude Bosentan (38 gm), isopropyl acetate (114 ml), ethanol (38 ml), and ammonium hydroxide solution (19 ml) were added and the mixture was heated to 55° C. to 60° C. for 30 minutes. The mass was cooled to 0° C. to 5° C. and maintained it at same temperature for 3 to 4 hours. The ammonium salt of Bosentan was filtered (30 gm) and it was washed with chilled isopropyl acetate.

Yield: 80%;
Purity: 99.7%; dimer impurity of formula (VI 0.05%; 6-hydroxy impurity of formula (VII): 0.06%.

The novel crystalline form of ammonium salt of Bosentan is characterized by its XPRD pattern having characteristic peaks at 5.96, 6.79, 9.09, 9.26, 10.52, 16.64, 17.60, 18.14, 18.53, 22.49, 24, 29, 24.91, and 27.5±0.2 degrees 2θ and XRPD pattern is as per FIG. 1.

We claim:
1. An ammonium salt of Bosentan (VIII)

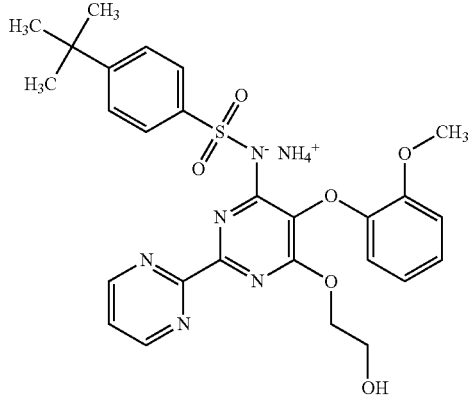

(VII)

comprising an XRD pattern having characteristic peaks at 5.96, 6.79, 9.09, 9.26, 10.52, 16.64, 17.60, 18.14, 18.53, 22.49, 24.29, 24.91, and 27.5±0.2 degrees 2θ as shown in FIG. 1.

2. An amorphous form of ammonium salt of Bosentan (VIII) comprising an XRD pattern as shown in FIG. 2.

3. A single pot process for the preparation of an ammonium salt of Bosentan (VIII)

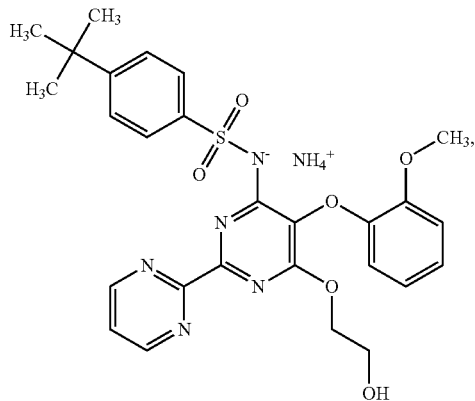

(VII)

the process comprising:
reacting 4,6-dichloro-5-(2-methoxyphenoxy)-2,2'-bipyrimidine (III)

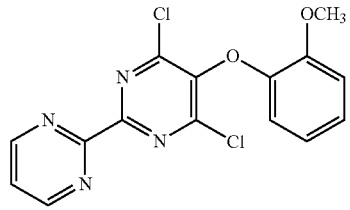

(III)

with 4-tert-butylbenzenesulfonamide (IV)

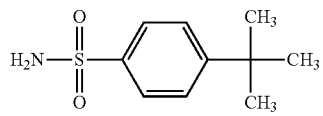

(IV)

in the presence of a solvent and a base; adding ethylene glycol to the reaction mass, maintaining the reaction mass at the temperature of between 50° C. and 150° C., until completion; and isolating the ammonium salt of Bosentan (VIII).

4. The process of claim 3, wherein the 4,6-dichloro-5-(2-methoxyphenoxy)-2,2'-bipyrimidine (III) is reacted with 4-tert-butylbenzenesulfonamide (IV) in the presence of a polar aprotic solvent selected from $C_3$-$C_6$ ketones; nitriles; $C_3$-$C_6$ amides; $C_2$-$C_8$ ethers; dimethylsulfoxide and combinations thereof and a base selected from sodium carbonate, potassium carbonate, sodium bicarbonate, potassium bicarbonate, cesium carbonate, calcium carbonate, sodium hydroxide, potassium hydroxide, cesium hydroxide, barium hydroxide, lithium hydroxide, and mixtures thereof.

5. The process of claim 3, wherein the isolation of the ammonium salt of Bosentan (VIII) is carried out by
a. cooling the reaction mass followed by addition of water and adjusting the pH of the reaction mass to pH 1 to 4 using acid and extracting the aqueous reaction mass by suitable organic solvent followed by concentrating the organic layer to obtain residue; and
b. adding a solvent and ammonia or ammonium hydroxide to the residue of step (a) and heating the obtained mixture until clear solution is obtained; followed by cooling the reaction mass, filtering and drying the ammonium salt of Bosentan (VIII).

6. The process of claim 5, wherein the acid used in step (a) is selected from tartaric acid, oxalic acid, mandelic acid, fumaric acid, acetic acid, formic acid, hydrochloric acid, nitric acid, sulfuric acid, hydrobromic acid, para-toluene sulfonic acid, or mixtures thereof, and the solvent used for extraction in step (a) is selected from aliphatic chlorinated hydrocarbons; hydrocarbons; $C_2$-$C_6$ alkyl acetates; and $C_2$-$C_8$ ethers.

7. The process of claim 5, wherein the solvent used to dissolve the residue in step (b) is selected from a $C_3$-$C_6$ ketone; an aromatic hydrocarbon; dimethylsulfoxide; a $C_1$-$C_5$ alkyl alcohol; acetonitrile; a $C_2$-$C_6$ alkyl acetate; a $C_2$-$C_8$ ether, water, and a base comprising ammonia, ammonium hydroxide, ammonium acetate, or ammonium carbonate, or combinations thereof.

8. The process of claim 5, further comprising purifying the ammonium salt of Bosentan (VIII) using a solvent, wherein the solvent is the mixture of isopropyl acetate, ethanol and ammonia.

9. A process for the preparation of an amorphous form of an ammonium salt of Bosentan (VIII)

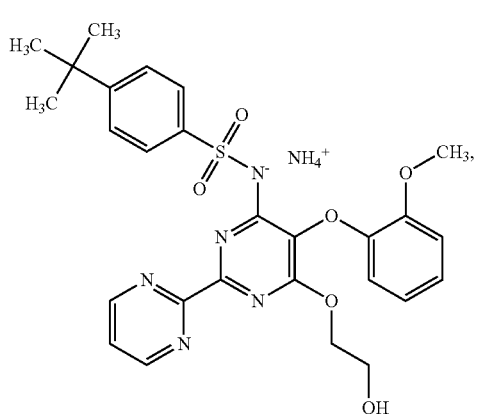

(VII)

said process comprising providing a solution of crystalline or a mixture of crystalline and the amorphous form of the ammonium salt of Bosentan in a solvent, removing the solvent to form a solid residue and isolating the solid residue to obtain the amorphous form of the ammonium salt of Bosentan (VIII).

10. A process for the preparation of a Bosentan (I)

the process comprising hydrolyzing an ammonium salt of the Bosentan (VIII)

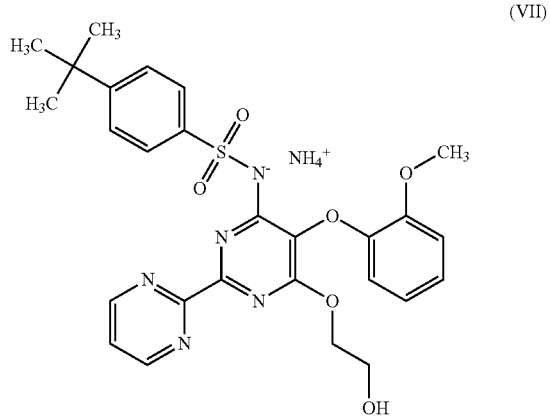 [SMILES: COc1ccccc1Oc1c([N-]S(=O)(=O)c2ccc(C(C)(C)C)cc2)nc(-c2ncccn2)nc1OCCO ; [NH4+]]

(VII)

by adding water to the ammonium salt, followed by adjusting the pH of the reaction mass to a value in the range of 1 to 6 using acid, extracting the Bosentan (I) from the hydrolyzed reaction mass using a solvent selected from a halogenated hydrocarbon; a $C_2$-$C_6$ alkyl acetate; a $C_2$-$C_8$ ether; a hydrocarbon, washing organic layer with water, distilling off the solvent under reduced pressure to obtain Bosentan formula (I) as residue.

11. The process of claim 10, further comprising purifying Bosentan (I) by treating it with a solvent selected from a nitrile; an alcohol; water or mixtures thereof and subsequently heating the mixture to reflux temperature followed by gradually cooling the mixture to 0° C. to 50° C.; maintaining the mixture at the same temperature for 30 to 60 minutes and isolating pure Bosentan of formula (I).

12. A process for the preparation of a Bosentan monohydrate (II)

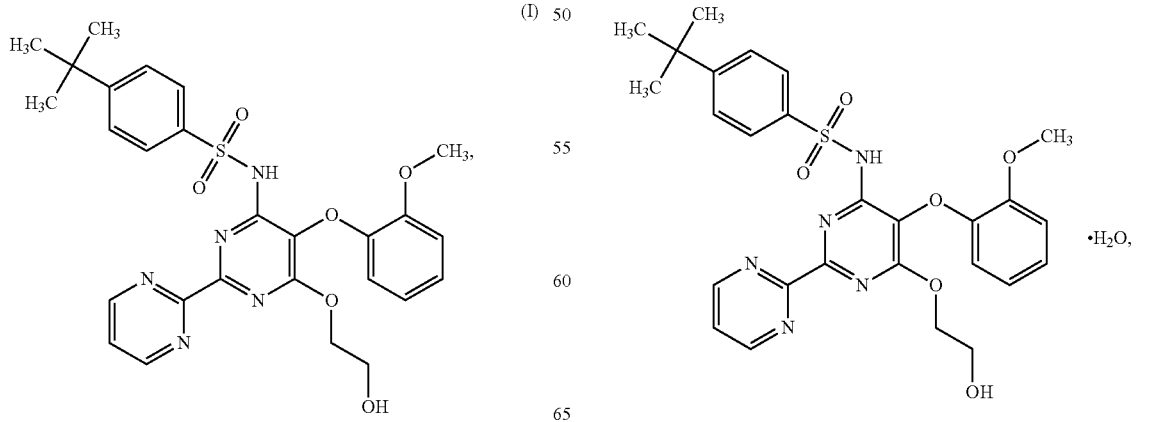

the process comprising dissolving Bosentan (I)

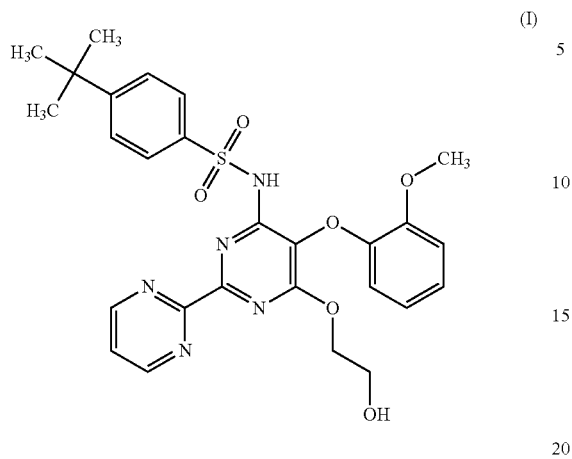

(I)

in a solvent; heating the mixture to get a clear solution, adding activated charcoal as decolorizing agent to the clear solution, continuing the heating followed by removing the activated charcoal by filtration; adding water to the filtered solution, cooling the filtered solution to 20° C. to 30° C. to precipitate the purified Bosentan monohydrate (II), and isolating highly pure Bosentan monohydrate (II).

13. The process as claimed in 12, wherein the solvent used in the preparation of the Bosentan monohydrate (II) is an alcohol comprising methanol, ethanol, propanol, or butanol.

* * * * *